US012778753B2

(12) United States Patent
Van De Graaf et al.

(10) Patent No.: US 12,778,753 B2
(45) Date of Patent: Nov. 3, 2026

(54) MEDICAL IMPLANT

(71) Applicant: Choice B.V., Eindhoven (NL)

(72) Inventors: Peter Van De Graaf, Sevenum (NL); Jorg Thomas Stroetzel, Venlo (NL)

(73) Assignee: Choice B.V., Eindhoven (NL)

(*) Notice: Subject to any disclaimer, the term of this patent is extended or adjusted under 35 U.S.C. 154(b) by 388 days.

(21) Appl. No.: 18/567,699

(22) PCT Filed: Jun. 8, 2022

(86) PCT No.: PCT/NL2022/050316

§ 371 (c)(1),
(2) Date: Dec. 6, 2023

(87) PCT Pub. No.: WO2022/260516

PCT Pub. Date: Dec. 15, 2022

(65) Prior Publication Data

US 2024/0277477 A1 Aug. 22, 2024

(30) Foreign Application Priority Data

Jun. 10, 2021 (NL) ...................................... 2028427

(51) Int. Cl.
*A61F 2/24* (2006.01)
*A61F 2/04* (2013.01)
*A61F 2/48* (2006.01)

(52) U.S. Cl.
CPC ............ *A61F 2/2476* (2020.05); *A61F 2/482* (2021.08); *A61F 2002/047* (2013.01); *A61F 2210/0033* (2013.01); *A61F 2250/0001* (2013.01)

(58) Field of Classification Search
CPC .............. A61F 2002/047; A61F 2/2476; A61F 2/0004; A61F 2/0036; A61F 6/24
See application file for complete search history.

(56) References Cited

U.S. PATENT DOCUMENTS 6,709,385 B2 * 3/2004 Forsell .................. A61F 2/0036
128/DIG. 25
7,758,542 B2 * 7/2010 Whalen ............. A61M 25/0017
604/103.01

(Continued)

FOREIGN PATENT DOCUMENTS

DE 102017121820 A1 3/2018
WO 2013144770 A2 10/2013
WO WO-2018130358 A1 * 7/2018 ........... A61F 2/0022

OTHER PUBLICATIONS

European Patent Office, International Search Report in corresponding International Application No. PCT/NL2022/050316, dated Sep. 20, 2022.

*Primary Examiner* — Eduardo C Robert
(74) *Attorney, Agent, or Firm* — Leydig, Voit & Mayer, Ltd.

(57) ABSTRACT

It is proposed to provide and implantable tube valve for implanting in a urinary tract, comprising: an implantable tube; a valve member mounted inside the tube and pivotable between an open position and a closed position and an actuator for pivoting the valve member; wherein the valve member comprises a pivot part, said pivot part formed as a single beak part; said valve member provided with a safety mechanism including a biasing element, an actuator, and the pivot part, wherein the beak part is arranged to pivot the pivot part towards the open position when a pressure exerted on the beak part exceeds a predetermined pressure.

10 Claims, 7 Drawing Sheets

(56) References Cited

U.S. PATENT DOCUMENTS

| | | | |
|---|---|---|---|
| 2012/0238803 A1 | 9/2012 | Lund | |
| 2014/0128666 A1* | 5/2014 | Shapiro | A61F 2/0036 600/30 |
| 2017/0095323 A1* | 4/2017 | Garcia | A61M 25/0127 |
| 2017/0281401 A1 | 10/2017 | van de Graaf et al. | |

* cited by examiner

MEDICAL IMPLANT

CROSS-REFERENCE TO RELATED APPLICATIONS

This patent application is a U.S. National Phase of PCT International Application No. PCT/NL2022/050316, filed Jun. 8, 2022, which claims priority to Dutch Application No. 2028427, filed Jun. 10, 2021, which are both expressly incorporated by reference in their entireties, including any references contained therein.

FIELD OF THE INVENTION

The invention relates to a medical implant that restores self-determined control of urinary flow lost due to illness, accident or other reasons.

DESCRIPTION OF THE PRIOR ART

Many types of artificial urethral sphincters are known for treating urinary incontinence. They are used when such remedies as the outpatient therapy, the pharmacological therapy and the pelvic re-education are not effective. The artificial urethral sphincters are used also as alternative to the traditional surgical techniques, which provide a reconstruction of the bladder support structures. Typically, such artificial sphincter can be provided by a valve structure to be implanted in the urethra, in particular, of a male or female patient, e.g. of a type disclosed in WO2013144770 which shows a variety of valve designs. A challenge for valve designs to be used as urethral sphincter is that the urinary tract may be contaminated by impurities, e.g. kidney and urinary stones. Patients suffering from incontinence problems may often be prone to other ailments and when suffering such conditions, the presence of an artificial sphincter may be problematic. Another challenge for dealing with incontinence issues is that the bladder, when not relieved, may rupture, which led to a serious health condition.

The invention aims to provide an implantable tube valve for implanting in a urinary tract comprising a valve member having a pivot part mounted inside the tube and pivotable between an open position and a closed position, that aims to mitigate such problems.

SUMMARY OF THE INVENTION

It is proposed to provide and implantable tube valve for implanting in a urinary tract, comprising: an implantable tube having an inner tube wall extending between two axial tube ends; a valve member mounted inside the tube and pivotable between an open position and a closed position and an actuator for pivoting the valve member between the open to the closed position; wherein the valve member comprises a pivot part constructed to pivot around a pivot axis oriented lateral relative to the tube; said pivot part formed as a substantially tubal orifice on side of the pivot axis, aligned, when in open position, to the tube, and said pivot part formed as a single beak part, on the other side of the pivot axis; the beak part having a sealing edge contacting the inner tube wall, when pivoted in the closed position, the valve member thereby closing off passage through the implantable tube; said valve member provided with a safety mechanism including a biasing element, actuator, and the pivot part, wherein the beak part is arranged to pivot the pivot part towards the open position when a pressure exerted on the beak part exceeds a predetermined pressure.

Another aspect of the invention concerns a system of a wireless charging device and an implantable tube device as herein disclosed.

BRIEF DESCRIPTION OF THE DRAWINGS

The invention will be further elucidated in the figures.

DETAILED DESCRIPTION

Figure 1:
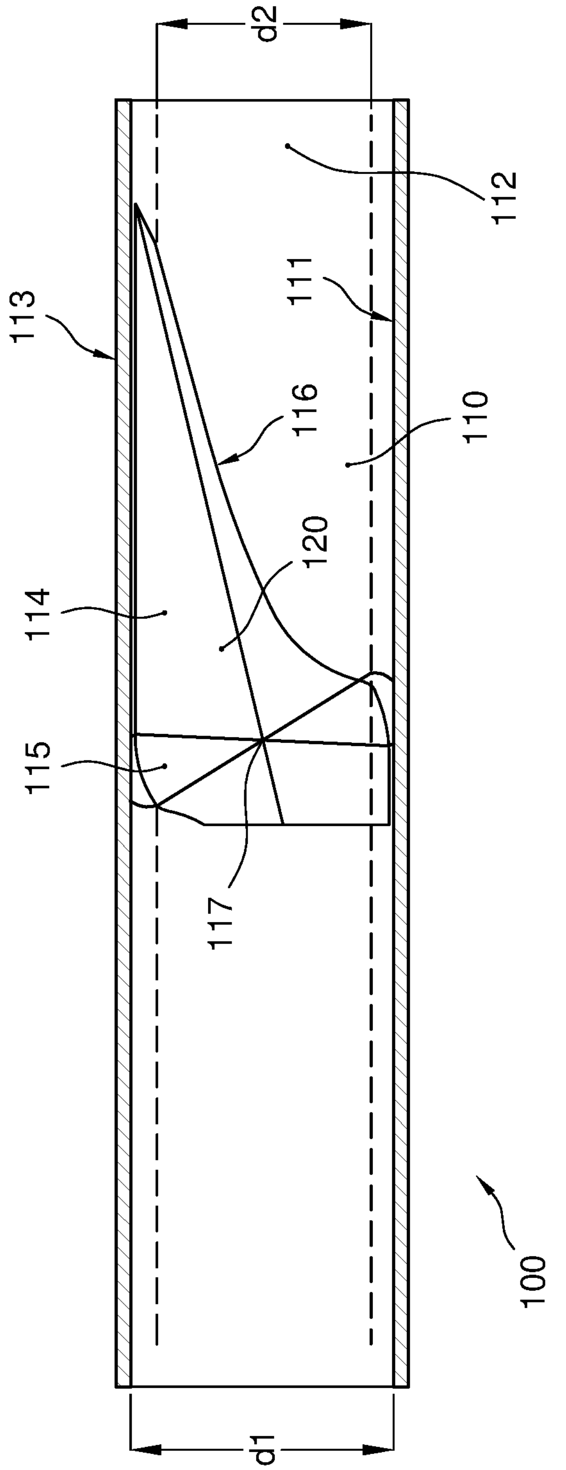
FIG. 1 shows an embodiment of an implantable tube valve for implanting in a urinary tract.

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms “a”, “an” and “the” are intended to include the plural forms as well, unless the context clearly indicates otherwise. The term “and/or” includes any and all combinations of one or more of the associated listed items. It will be further understood that the terms “comprises” and/or “comprising” specify the presence of stated features but do not preclude the presence or addition of one or more other features. All publications, patent applications, patents, and other references mentioned herein are incorporated by reference in their entirety. In case of conflict, the present specification, including definitions, will control.

The term “mount” is used in its ordinary meaning to emphasize that many mounting arrangements are possible. These arrangements include physical shaft mounts, ball bearing mounts or any other mechanical arrangement providing a rotational degree of freedom for the valve member mounted in the mount. The rotational degree of freedom defines an axis of rotation or pivot axis that is transverse to the implantable tube. Preferably, the mount is formed partly by the tube, and a corresponding mount part formed by the valve member.

The term “conformal to” is used in its ordinary meaning to indicate the form following nature of the identified features, meaning that shape and size are similar for a substantial part of said features. In mathematical sense the meaning conformal indicates that the features preserve shape on a local scale. To illustrate that some deviation may be allowed, depending on the specifics of the application it is considered that certain features, e.g. a valve member's outer and inner face are considered conformal if a thickness between the two varies with e.g. less than 10%.

In stricter sense, it is considered that 'contiguous to' means that the form is not only similar, but identical so that there virtually no or only a very small gap between the two features, e.g. less than 0.1 mm. In a more abstract sense, the term 'coincides with' is used to indicate that a feature is enveloped by a notional feature coinciding with an outer face over a substantial part of said feature.

By the term 'extending continuously' e.g. between axial tube ends, it is indicated that there are no substantial deviations present between said extensions, notably no or very limited protruding outer features, in respect of the implantable tube. In particular, the implantable tube extending continuously between the axial tube ends indicates that there is no or very limited spatial deviation from the tube form along the entire tube. The term continuous does nevertheless not preclude the presence of minor protrusions or depressions, e.g. for forming an actuator housing, sealing edge, mounting or valve seat on a smaller scale or for forming a rugged surface e.g. for fixed insertion in the human vessel, e.g. in the form known for stents. It is indicated on a larger scale that the general flow through the object may be unobstructed due to the tube's continuous form, or that the object itself does not substantially deviate from a tube form. In particular, depending on its application, the actuator actuating the valve member is shaped in elongated form along the tube in a way that can be absorbed by stretching the surrounding tissue, e.g. the urinary tract.

A 'heating circuit' may comprise one or more analog or digital hardwire elements configured to perform operational acts in accordance with the present systems and methods, such as to provide control signals to the various other module components. The processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include micro-controllers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

While example embodiments are shown for systems and methods, also alternative ways may be envisaged by those skilled in the art having the benefit of the present disclosure for achieving a similar function and result. E.g. some components may be combined or split up into one or more alternative components. Finally, these embodiments are intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims.

Any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage.

In FIG. 1, there is illustrated an embodiment of an implantable tube valve device 100 for implanting in a urinary tract. The tube valve 110 may be implanted by means of a catheter insertion. Similarly, the device may be implanted in other vessels such as the vas deferens, bowels or urinary ducts, for example to counter incontinency problems or any tube transporting fluids or (micro) particles. This is achieved by an implantable tube having an inner tube wall 111 of a diameter d1, e.g. of 2-8 mm, and an outer tube wall of e.g. 3-10 mm. The inner wall extends between two axial tube ends 112; and a valve member 120 mounted inside said tube 110 and pivotable between an open position and a closed position. The valve device 100 has as an advantage its unobstructed flow through the tube when pivoted in open position in an inner diameter d2, e.g. with a diameter of 2-8 mm. In FIG. 1, the valve member 120 is illustrated in an open position. The outer face extends along a beak part 114 and a pivot part 115 and is conformal to the inner tube wall 111. The valve member 120 comprises a sealing edge 116 contacting, the inner tube wall 111 when pivoted in the closed position thereby closing off passage through the implantable tube 110. For ease of understanding, an actuator for pivoting the valve member 120 between open to the closed position is not shown. In the shown embodiment a mount may be formed by opposite shaft members (not shown) protruding from the valve member through the tube wall thereby forming an axis of rotation, or other suitable mounting arrangements.

Figure 2A:
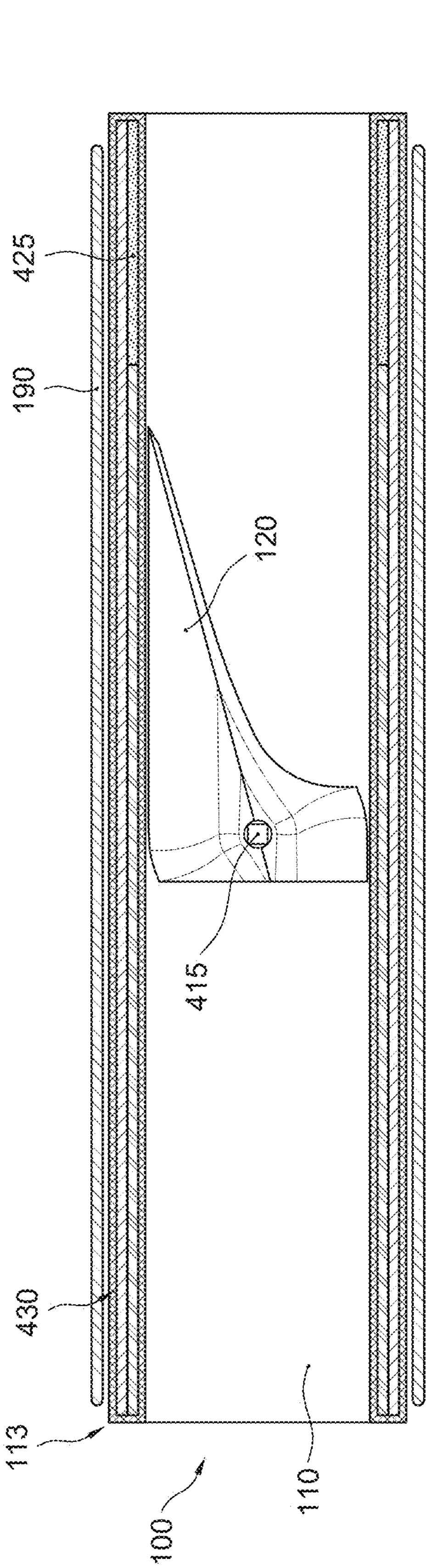
FIGS. 2A and 2B show a pivotable cam member for mounting to a pivot shaft.
Figure 2B:
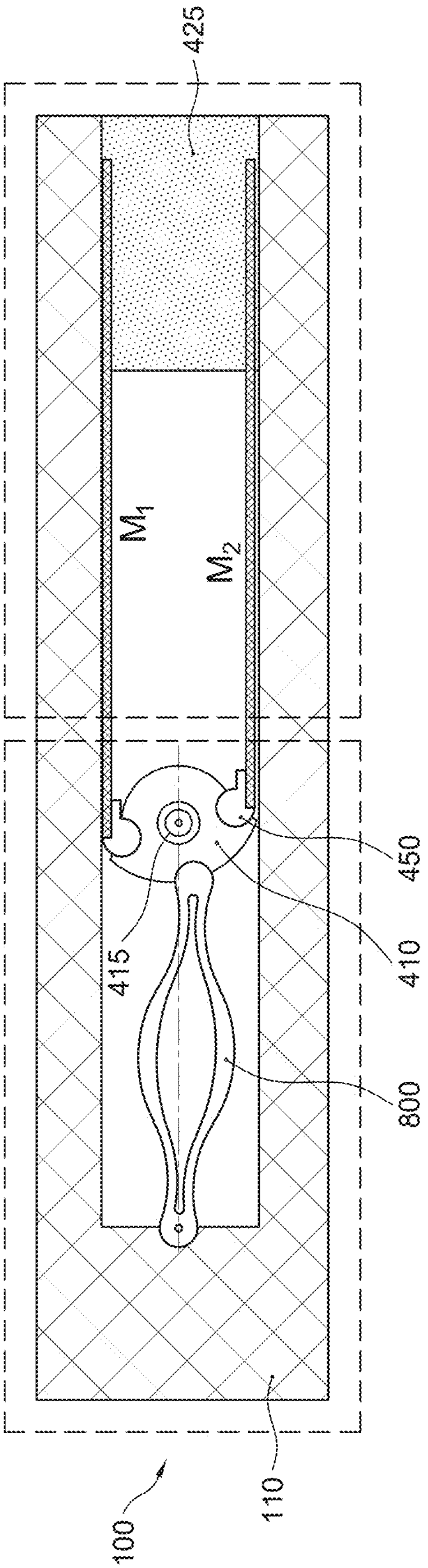

Turning now to FIGS. 2A and 2B, pivotable cam member 410 preferably is shown having a central hole for mounting to pivot shaft 415 in connection with pivot part 115 (see FIG. 1). The pivotable cam member 410, in the shown example, comprises cylindrically rounded cutouts for mounting the actuator connectors 450 at a radial distance from the pivot shaft 415, however the pivotable cam member 410 may be a differently shaped body suitable for a transmission of actuation forces into an actuation torque on the pivot shaft 415, e.g. a body containing one or more cranks or levers. In the closed position, pivot part 115 will be kept closed with a bias force, that is provided, for example, by a biasing element 800 connected to the pivotable cam member 410 and arranged for preloading the pivotable cam member 410 to bistably bias the valve member 120 towards the open or closed position. The pivot shaft 415 rotates the valve member 120 between an open position and a closed position.

Pivotable cam member 410 is preferentially designed as a separate part on the outside of the tube 110, leading to only a very minute extension of the tube contour 113 in lateral direction. The pivotable cam member 410 may be designed having a curved inner and outer surface concentrically aligned with the tube 110 to further limit the extension of the tube contour 113.

Heating circuit 425 is preferably geared to a wireless charging device (not shown) but may also be powered by other means, e.g. a battery pack etc.

An external control unit may establish a wireless connection to the implant, supplies the power and the control signals for opening and closing. The implant itself may or may not have a power storage and will be inactive between switching operations. For wearers with limited endogenous control capabilities, it is possible to imagine the control unit giving a signal at equidistant intervals when the bladder should be emptied. For wearers who are in medical or similar facilities, the control unit may enable a connection, to be defined in more detail, to a higher-level patient management system in order to inform the staff of the pending bladder emptying.

In the shown embodiment the heating circuit comprises a charging capacitor (not shown) electrically connected to a charging antenna 430 (FIG. 2A) arranged along the implantable tube valve 100. The heating circuit 425 comprises corresponding logic to heat a first or second tension wire $M_1$, $M_2$ when the charging capacitor is charged with a threshold charge, e.g. charged by the charging antenna 430.

The logic may have further gearing options, e.g. a (wireless) readout, such as status check options or reset options, and is preferably operated by a coded signal that only activates the heating circuit 425 when a corresponding security code is transmitted. In its simplest form, the wireless charging system functions as a bistate switch, switching the valve member 120 from open to closed position or from closed to open, depending on the initial arrangement.

The outer surface of the tube 110 may be covered by a foundation 190, comprising a material that facilitates adhesion to the lumen of the human vessel the implantable tube valve 100 is implanted in, such as a biocompatible meshed, porous or fabric material. Alternatively, the foundation 190 or tube 110 may comprise radially extending protrusions, e.g. spikes or hooks that form a mechanical bonding with the surrounding tissue, thereby fixating the implantable tube valve 100 to the vessel lumen.

The tension wires M1, M2 may reversibly contract when heated by the heating circuit and expand when cooled, thereby providing an actuation force to the pivotable cam member 410. Alternatively, the tension wires M1, M2 may reversibly expand when heated by the heating circuit and contract when cooled. Preferably, the tension wires $M_1$, $M_2$ are of a form that contracts when heated. Shape metal alloy suitable for such may for instance be a NiTi alloy known as Nitinol, but other shape metal alloys can be used to purpose.

The actuation force may be provided by the tension wires M1, M2 being directly coupled to the pivotable cam member 410, e.g. by being soldered, welded, glued or threaded to each other. Preferably, at least one of the tension wires M1, M2 is coupled to a connector, with said connector being mounted in the pivotable cam member 410. For example, each of tension wires M1, M2 may be mounted to the pivotable cam member by means of actuator connector 450. The actuator connector 450 may comprise a cylindrically rounded end engageable with a cylindrically rounded cutout on the pivotable cam member to form a rotatable connection. A benefit of having a cylindrically rounded contact surface between the actuator connector 450 and the pivotable cam member 410 may be that the actuation force on the actuator connector 450 is exclusively converted into a torque on the pivotable cam member 410, which may facilitate maintaining proper alignment between the pivotable cam member and the actuator connector. Conversely, in e.g. a conical contact surface, the actuation force is converted into a torque as well as an axial force, possibly destabilizing or locking the connection between the pivotable cam member 410 and the actuator connector 450. The actuator connector 450 may be an integrally formed part of the tension wires M1, M2. Alternatively, the actuator connector 450 may be a separate part which is assembled to each of tension wires M1, M2 e.g. by soldering, welding, gluing or threading.

Tension wires M1, M2 may be mechanically connected to at least two respective terminals (+) (−) of the heating circuit at one end, to provide a current running therethrough, and mechanically connected to the pivotable cam member 410 at another end, so that the current runs through the tension wire M1 and M2 respectively, without branching off to the pivotable cam member 410. Each of the tension wires M1, M2 may be electrically connected to a positive and a negative terminal on the heating circuit 425, such that a closed current loop is formed without current passing from the connector 450 to pivotable cam member 410. This has as benefit, that no currents pass from connector 450 to pivotable cam member 410, ensuring that connectors 450 can be freely mounted without running into fixation by microwelds that would arise from such currents.

Figure 3A:
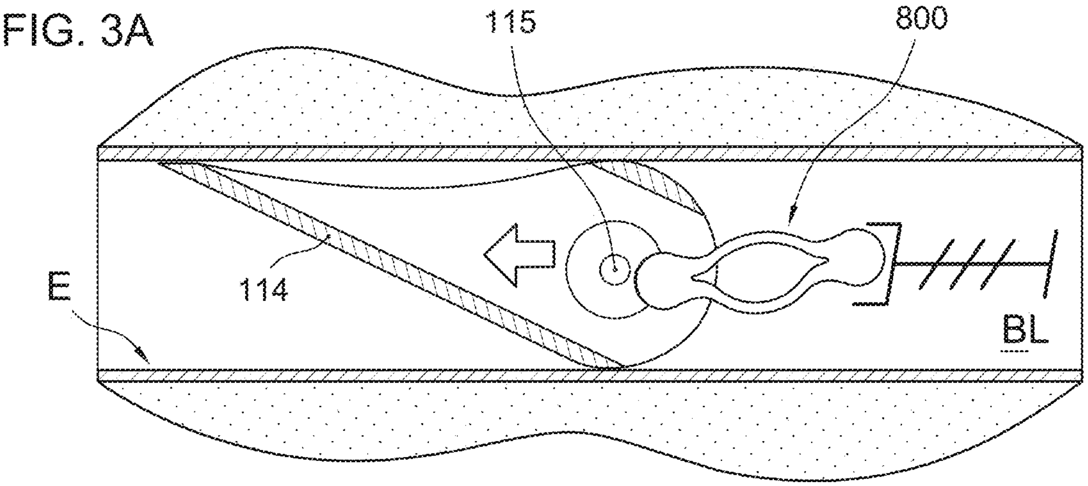
FIGS. 3A, 3B and 3C show the valve member provided with a safety mechanism.
Figure 3B:
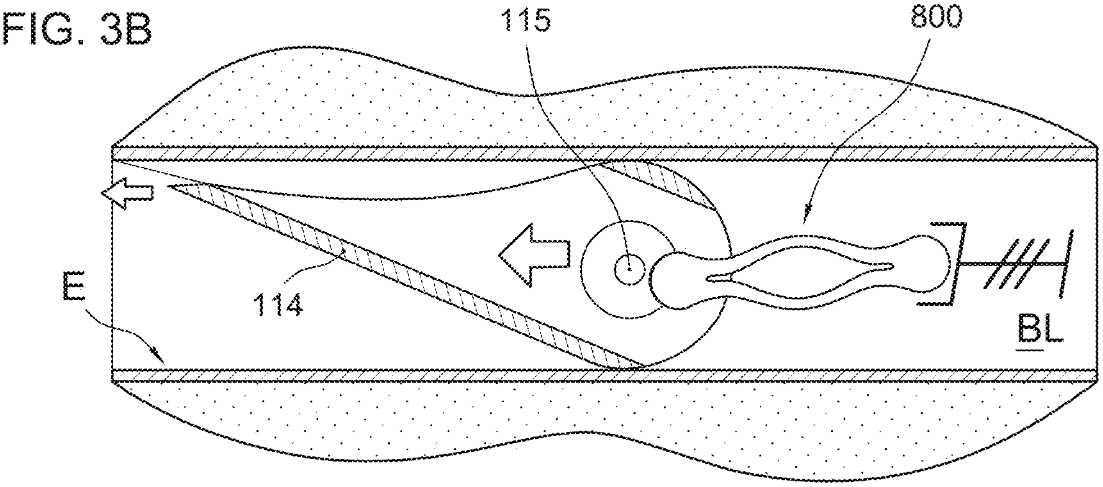
Figure 3C:
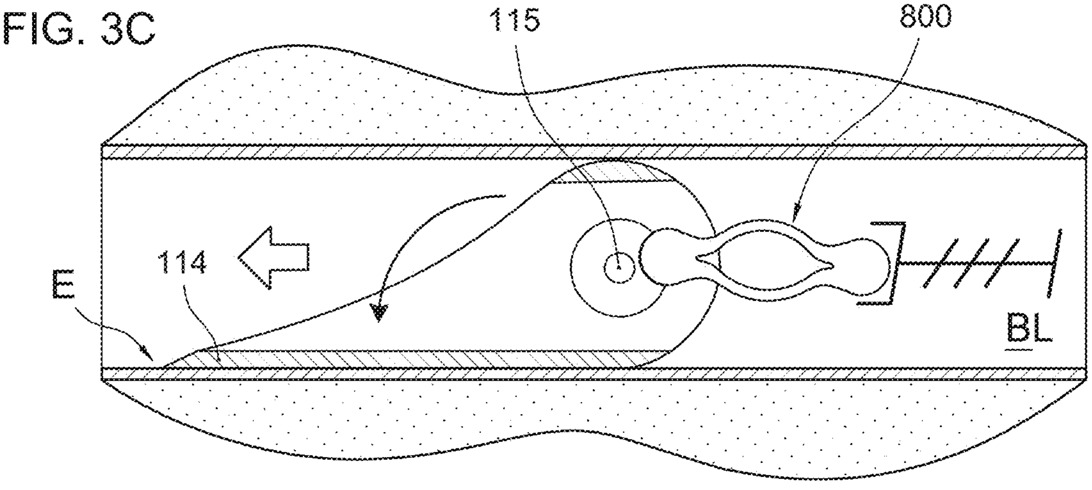

FIGS. 3A-C show an essential aspect of the invention, namely, that the valve member depicted in FIGS. 1 and 2A-B is provided with a safety mechanism including the biasing element 800, and the pivot part 115 wherein the beak part 114 is arranged to pivot the pivot part 115 towards the open position when a pressure exerted on the beak part 114 exceeds a predetermined pressure. The safety mechanism also includes the actuator design, that may be mechanically decoupled when not active, or at least may not obstruct the rotation of pivot part 115. Pivot part 115 and a beak part 114 are thus designed to exert a torque that pivots the pivot part 115 to an open position. Such a design can for example be provided by taking advantage of the asymmetric design of the beak part 114 relative to pivot part 115. Biasing element 800 may be connected to the pivot cam member 410 and arranged for bistably biassing the valve member 120 towards the open or closed position. When the pressure in bladder BL exceeds a certain threshold, e.g. is larger than 1.2 Bar. Pivot part 115 is designed, together with biasing element 800 to mechanically comply with the exerted pressure, and a torque is provided by pressure exerted on the asymmetric beak part, that rotates the pivot part 115.

Initially, as depicted in FIG. 3A, while a certain torque is provided by the beak part 114 in response to the bladder pressure, the torque is too small to counteract the biasing force exerted by biasing element 800, and beak part remains in closed position.

When a pressure is increased the torque will increase also that is exerted by the beak part 114 to counteract the biasing element 800. This will result in a partial opening of the beak part 114, to relieve some of the pressure and keep the bladder pressure below a threshold pressure which is important for the safety of the patient, as a bladder rupture due to overpressure may have life-threatening consequences.

Depending on the design of the biasing element, a bistable characteristic of the biasing element (e.g.: by a snap force design) may result in (sudden) yielding of the beak part to the open position, depicted in FIG. 3C. In this case, the bladder is empties and no remaining pressure will be there.

The depicted steps of FIGS. 3A-C are in addition to a voluntary movement of the valve member from a closed position to an open position, by actively pivoting pivot part 115 by an actuator, e.g. of a design depicted in FIG. 2B. Thus, the steps depicted in FIGS. 3A-C will be carried out in emergency conditions irrespective of a voluntary movement initiated by an actuator, but follow from a constructional design that is arranged to exert a torque that pivots the pivot part when exceeding a threshold pressure, whether the user of the tube valve is actively controlling the valve member via an actuator input. This may be caused when e.g. the feeling of a filled bladder is missing, the person is unconscious or the external device to control the actuator is not available or inoperative.

Figure 4:
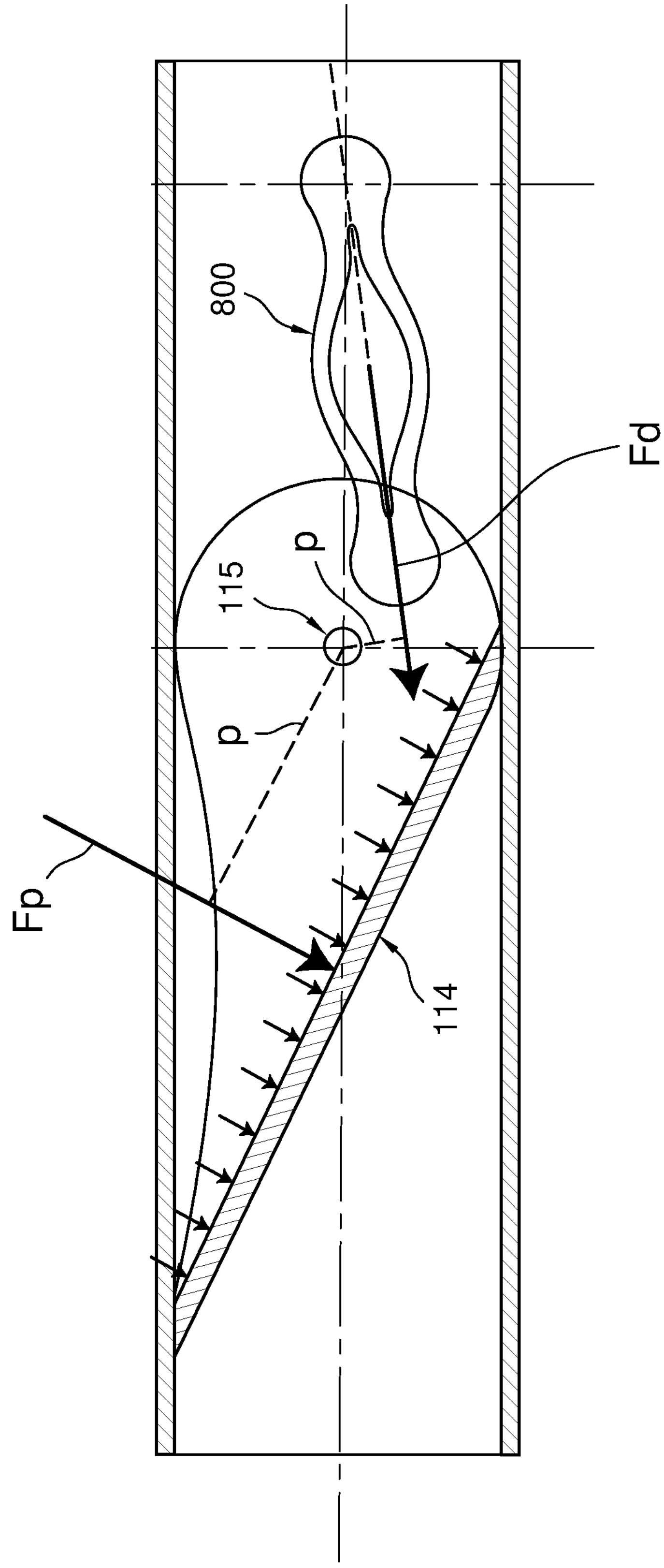
FIG. 4 shows a detailed sample calculation for designing the safety mechanism.
Figures 5A, 5B, 5C, 5D:
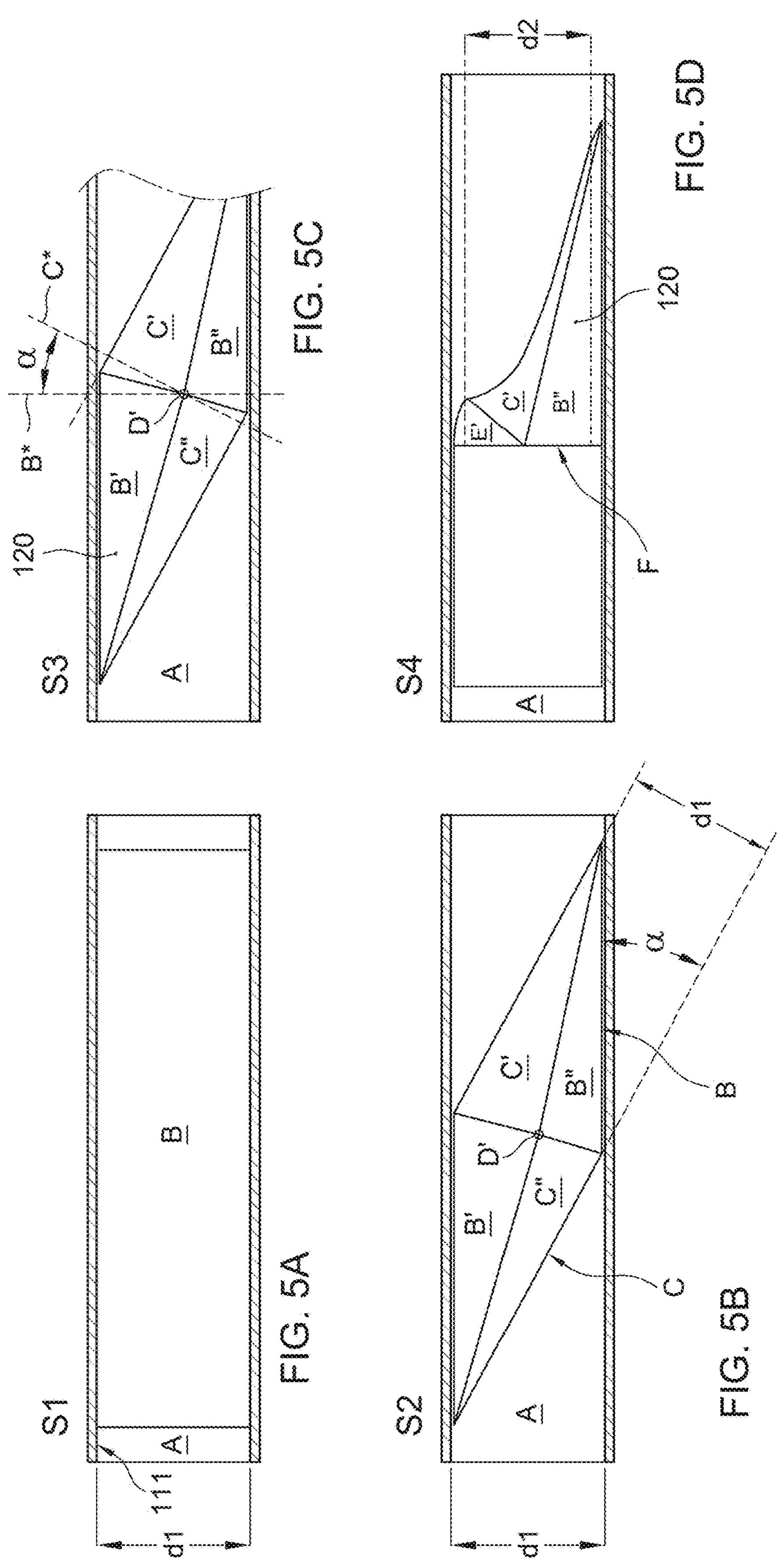
FIGS. 5A-D show in detail a method of constructing the valve member disclosed.

FIG. 4 shows a detailed sample calculation for designing the safety mechanism. The calculation is based on the insight that the biasing element 800 should not only be designed to a desired preloading force to the pivotable cam member 410 to bistably bias the valve member towards the open or closed position; but should also be designed to pivot the pivot part towards the open position when a pressure exerted on the beak part exceeds a predetermined pressure. For example, in case an overpressure of 1.2 bar is taken as a threshold, this means that a difference pressure is 0.2 bar.

For a practical dimensioning an exemplary tube inner having diameter of 7 mm and a beak part angle of alpha 30 degrees, this amounts to an elliptical area having a length axis of $a=d/2\ \tan(\text{alpha}/2))$ which amounts to about 13 mm.

which amounts to a projected area of $A=\text{pi}\ a\cdot d$ and an effective force contact point eccentric to the rotational axis of $x=4a/3\ \text{pi}$ A resultant torque would than be given by $M=p\cdot A\cdot x$; which can be substituted to $$M = p\cdot\frac{d^3}{12((\tan(\text{alpha}/2))^2}$$

A resultant maximum torque, for d=7 mm; alpha is 30 degrees and a pressure difference of 0.2 bar could amount to $7.9\cdot10^{-3}$ N·m, to be provided to by the biasing element 800.

The biasing element 800 provides a counter torque that is determined by the beak angle in closed position, and a resultant biasing force exerted by the bias member to the pivot member, resulting in a torque that can be expressed as $Fd*d$ where Fd is a biasing force and d is the effective arm, depending on the effective force contact point eccentric to the rotational axis of the pivot part.

This force is the 'safety force' that safely holds closed the beak part in closed position, and is dependent on the extent of the beak part, since the resultant torque exerted by pressure force is dependent on the length of the beak part 114, that results in an effective arm p and corresponding torque $Fp*p$ where Fp is the effective force developed by the difference pressure and dependent on the projected area of impact, and arm p which are both dependent on the length of the arm.

In case $Fp*p>Fd*d$, the pivot part 115 will pivot towards the open position.

FIGS. 5A-D show in detail a method of constructing the valve member disclosed in FIG. 1 from known shapes such as cylinders and spheres. In actual construction, for example, the valve member may be formed by machining, moulding or 3D printing techniques.

In a first step S1 (see FIG. 5A) one starts with a hollow tube body A with inner diameter d1 filled with a first notional body B also with diameter d1. Accordingly, a solid inner body is formed as an inner member contiguous to the tube wall 111. In a second step S2 (see FIG. 5B) first notional body B is intersected with a second notional body C also of diameter d1 under an angle alfa, resulting in a remaining intersection body of first notional body B and second notional body C. Valve member, in particular its sealing edge is thus formed by an intersection curve of the first and second notional bodies B and C, the first notional body B coinciding with the inner tube wall of hollow tube body A and the second notional body C formed by pivoting the first notional body B over the pivot axis D. First notional body B is thus cut off by an intersecting shape of the second notional body C of the same shape as the hollow inner cylinder but that is angled relative to the longitudinal axis of the hollow tube body A.

In this way pivot point D' is created on an intersection curve between four segments B', B", C', C" resulting in stable positions within hollow tube body A. The respective angle alfa between longitudinal axes of hollow tube body A and the shape of the second notional body C defines the rotation angle of the valve member thus formed.

In a third step S3 (see FIG. 5C) section C* is pivoted towards section B*, around pivot point D', such that there is no material outside the rotation, and the cylinder surfaces of first notional body B smoothly transfers into cylinder surface of second notional body C via a further notional body D coinciding with sphere segments E' and E" forming a pivot part. The valve member 120 can now rotate between the two positions B* and C* over rotation angle alfa. By shaping a pivot part in sphere form a rotation axis is defined. Pivot part forms a transition area between the two angled cylinder forms of first notional body B and second notional body C so that the valve member has a sealing edge with an edge face 115-3 proximal to the pivot points that coincide with the further notional body D formed by pivoting the intersection curve B* towards C*. In this way, the segments E' and E" deviate from the cylindrical forms of first notional body B and second notional body C, so that the valve can smoothly pivot without a gap inside the tube inner wall or with only a very small gap. To further prevent urine or other watery fluids to enter the gap between valve member and inner tube wall, these or parts thereof may be formed by a hydrophobic material.

In fourth step S4 (see FIG. 5D), the valve member 120 is completed by removing one of the segments B' and cutting out inner cylinder F, collinear with the first notional body B, with a diameter d2. Segments B" and C' are still cylinder surfaces, E' is still a sphere segment.

Figure 6A:
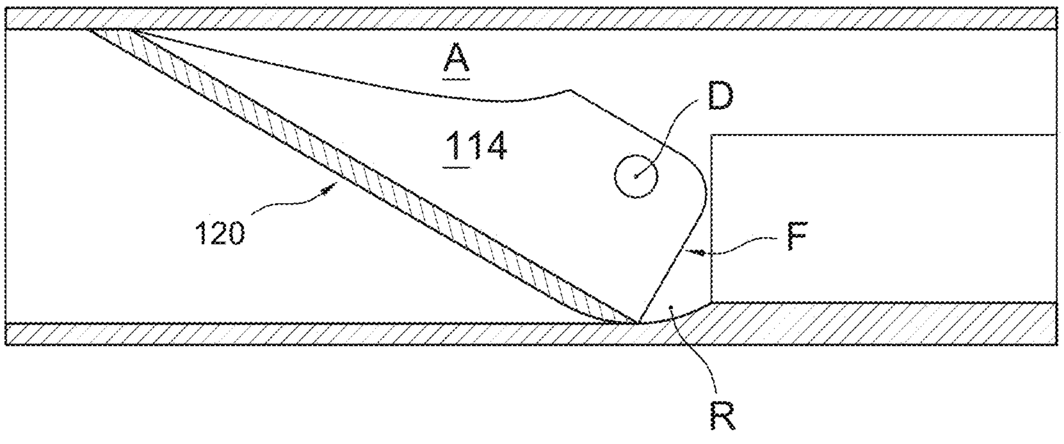
FIGS. 6A-C shows an additional embodiment.
Figure 6B:
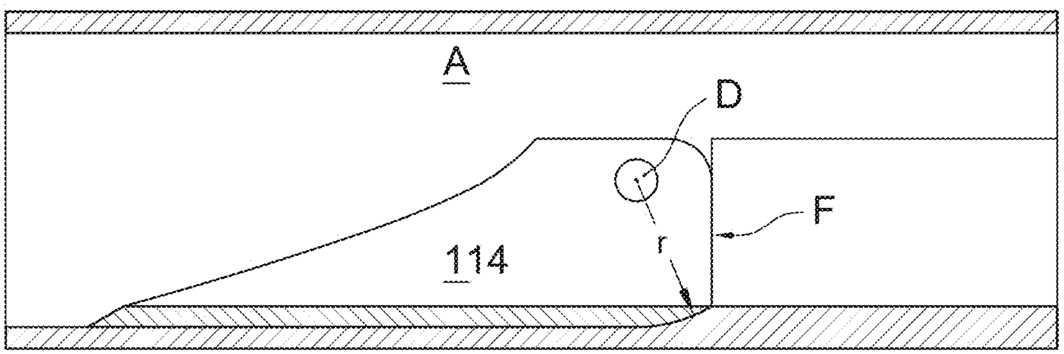
Figure 6C:
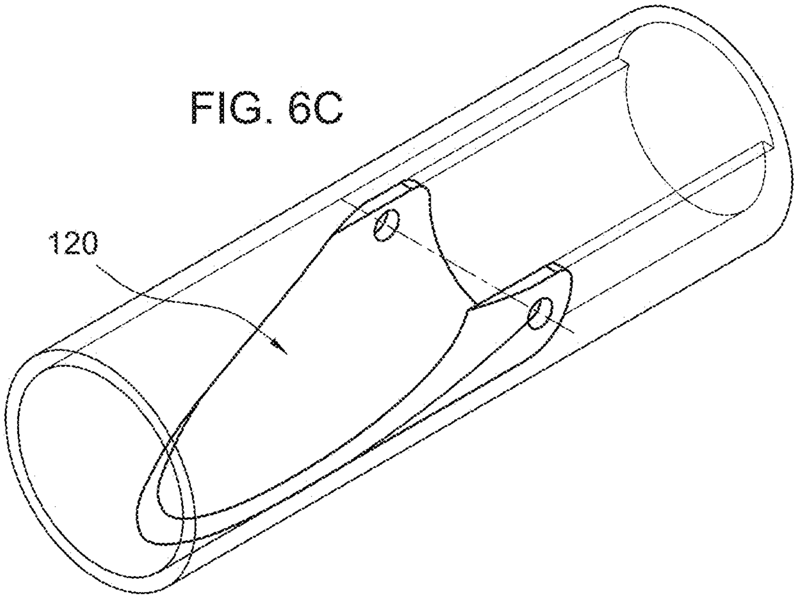

FIG. 6A shows an additional embodiment having a single beak part in closed position. In this case, the pivot part has a semi circumferential rear edge F, which only follows part of the circumference of the inner tube wall A. Pivot part is at least partly embedded, in open position, in a recess R provided in the outer wall, so that the semi circumferential rear edge aligns with an inner tube wall. In FIG. 6B the beak part is aligned, in open position, with an inner wall of the hollow tube body A. To this end the inner wall may have a recess that conforms to the single beak part 114, wherein the beak part slightly extends beyond a pivot axis D to a largest radius r spanning a rear edge F of the beak part 114 to the pivot axis. In this case rear edge F only follows a part of the tube wall over a semi halve circumference and does not form a closed cylinder shape. With pivot axis D still tightly in connection with a cam axle (not shown) that allows pivoting of the beak part, may optimize a beak shape to be fully embedded in the inner wall of the tube to optimize a flow cross section of the valve member 120. FIG. 6C shows a perspective view of valve member 120.

Figure 7A:
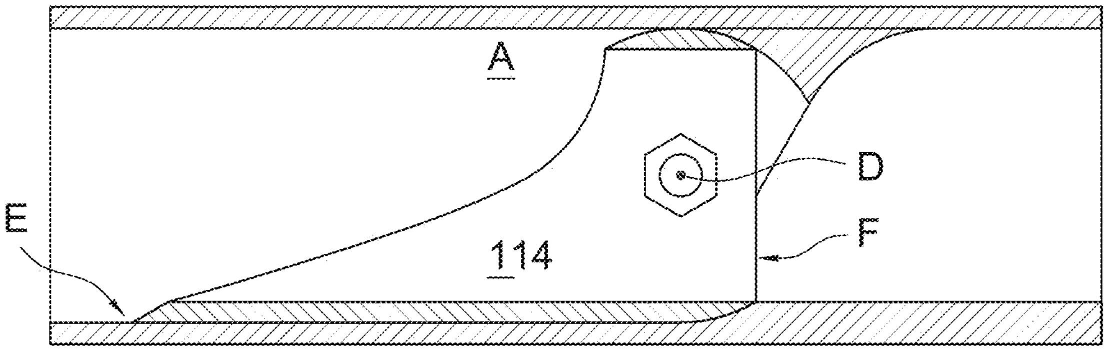
FIGS. 7A and 7B show a further alternative embodiment of the implantable valve tube.
Figure 7B:
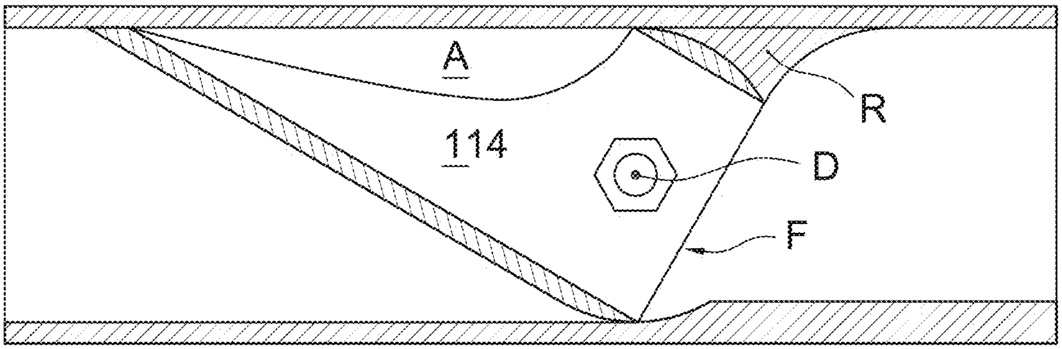

FIGS. 7A and 7B show a further alternative embodiment of the implantable valve tube that may allow rotation of the pivot part. In this case valve member 120 has a sealing edge E that follows a substantially planar contour and has an elliptical form. The pivot part has a circumferential rear edge F that pivots against a protruding ridge R provided on the inner tube wall.

Pivot part may be sphere shaped and rear edge F of beak part 114 follows a full circumference of the inner tube wall of hollow tube body A. Protruding ridge part R may aligns with rear edge F of the beak part 114. The ridge part R limits the cross section of inner wall of hollow tube body A but at the same time forms a spherical contact face for rotation of pivot part. Ridge part R may prevent small debris entering the rotating outer face of the pivot part. Ridge part R only extends over an outer semi halve circumference of the tube wall. The arrangements depicted in the embodiments are formed by three major constituents, notably, a valve member, actuator arrangement and powering device. These elements may be combined to benefit to provide the tiny dimensions of an implantable tube, but may be used separately for other applications, notably, valve arrangements that provide larger passage through the implantable tube where the actuator may be formed by other means. Also, the embodiments were directed to idealized shapes, but in practice may be suitably (de) formed e.g. in round, not necessarily circular forms and rotation symmetric, not necessarily spheric shapes but aspheric shapes for example, ellipsoid shapes. Further aspects of the invention are formed by an implantable tube as described in the above wherein the mount is formed by opposite shaft members protruding from the valve member through the tube wall thereby forming an axis of rotation. The heating circuit may be geared to a wireless charging device, the heating circuit electrically connected to a charging capacitor and a charging antenna arranged along the implantable tube; and wherein the heating circuit comprises logic to heat a first or second tension wire when the charging capacitor is charged with a threshold charge, charged by the charging antenna.

The invention claimed is:

1. A urinary tract tube valve configured for implanting in a urinary tract, the urinary tract tube valve comprising:
- a tube having an inner wall forming a lumen extending between two axial tube ends;
- a valve member mounted inside the tube and pivotable between an open position and a closed position; and
- an actuator for pivoting the valve member between the open position and the closed position;
- wherein the actuator is provided with a biasing element to bias the valve member in the open position or the closed position,
- wherein the valve member comprises a pivot part;
- wherein the pivot part is constructed to pivot within the lumen around a pivot axis oriented lateral relative to the lumen;
- wherein the pivot part is formed as:
  - a substantially tubular orifice on a first side of the pivot axis, and
  - a beak part on a second side of the pivot axis;
- wherein the substantially tubular orifice, with the pivot part in the open position, is aligned with the inner wall forming the lumen of the tube;
- wherein the beak part has a sealing edge configured for contacting the inner wall such that, when the valve member is in the closed position, the valve member closes off the lumen of the tube thereby preventing passage of fluid through the tube; and
- wherein the valve member is provided with a safety mechanism using a combination of the biasing element, the actuator, and the pivot part such that the beak part is arranged to pivot the pivot part towards the open position when a pressure exerted on the beak part exceeds a threshold pivot actuation pressure.

2. The urinary tract tube valve of claim 1, wherein the beak part of the pivot part further comprises an outer face conformal and contiguous to the inner wall when the pivot part is pivoted in accordance with the valve member in the open position; and
- wherein the beak part comprises an inner face conformal to the outer face thereby providing unobstructed passage through the lumen of the tube, when the pivot part is pivoted in accordance with the valve member in the open position.

3. The urinary tract tube valve according to claim 2, wherein the inner face conforms to the outer face with a thickness that varies less than 10%.

4. The urinary tract tube valve according to claim 1, wherein the pivot part has a circumferential rear edge that pivots against a protruding ridge provided on the inner wall.

5. The urinary tract tube valve according to claim 1, wherein the pivot part has a semi circumferential rear edge, and
- wherein the pivot part is at least partly embedded, with the valve member in the open position, in a recess provided in the inner wall of the tube, so that the semi circumferential rear edge aligns with the inner wall.

6. The urinary tract tube valve according to claim 1, wherein the beak part extends from the pivot axis and is formed by an intersection curve of a first notional body and a second notional body,
- wherein the first notional body coincides with the inner wall, and
- wherein the second notional body formed by pivoting the first notional body over the pivot part.

7. The urinary tract tube valve according to claim 6, wherein the pivot part has a proximal edge face coinciding with a third notional body formed by rotating an intersection curve proximal to the pivot axis.

8. The urinary tract tube valve according to claim 7 wherein the tube has a cylindrical inner wall extending continuously between the axial ends;
- wherein the first notional body is a cylinder forming an intersection curve with the inner wall when the pivot part is pivoted in accordance with the valve member in the closed position, and
- wherein the third notional body is a sphere.

9. The urinary tract tube valve according to claim 1, wherein the actuator comprises:
- a pivotable cam connected to the valve member; and
- a bistable pivot mechanism that is pivotable under the influence of an excess force exerted to the pivotable cam.

10. The urinary tract tube valve according to claim 9, wherein the actuator comprises:
- a mounting structure, and an actuating member pivotable relative to the mounting structure, wherein the mounting structure has an axis of elongation further comprising:

a heating circuit; and first and second tension wires aligned along the axis of elongation, wherein the tension wires are formed of a shape metal alloy, connected to the heating circuit and eccentrically engaging the actuating member, thereby pivoting the actuating member to positions relative to the mounting structure, so that, in use, the actuating member is pivoted in a first position by heating the first tension wire and the actuating member is pivoted in a second position by heating the second tension wire.

* * * * *